(12) United States Patent
Stahl et al.

(10) Patent No.: US 7,972,489 B2
(45) Date of Patent: Jul. 5, 2011

(54) SENSOR ELEMENT

(75) Inventors: Roland Stahl, Freiberg (DE); Hans-Martin Wiedenmann, Stuttgart (DE); Berndt Cramer, Leonberg (DE); Detlef Heimann, Gerlingen (DE); Thomas Wahl, Pforzheim (DE); Lothar Diehl, Gerlingen (DE); Thomas Moser, Schwieberdingen (DE); Bjoern Janetzky, Ditzingen (DE); Jan Bahlo, Pforzheim (DE)

(73) Assignee: Robert Bosch GmbH, Stuttgart (DE)

( * ) Notice: Subject to any disclaimer, the term of this patent is extended or adjusted under 35 U.S.C. 154(b) by 1825 days.

(21) Appl. No.: 10/947,617

(22) Filed: Sep. 22, 2004

(65) Prior Publication Data

US 2005/0087443 A1 Apr. 28, 2005

(30) Foreign Application Priority Data

Sep. 29, 2003 (DE) .................. 103 45 143

(51) Int. Cl.
*H03H 7/00* (2006.01)
*G01N 27/26* (2006.01)
(52) U.S. Cl. ........ 204/428; 204/424; 204/427; 204/412; 73/23.2; 73/31.05; 95/201
(58) Field of Classification Search ............... 204/424, 204/427, 412, 428; 73/23.2, 31.05; 95/201
See application file for complete search history.

(56) References Cited

U.S. PATENT DOCUMENTS

| | | | | |
|---|---|---|---|---|
| 4,859,307 A * | 8/1989 | Nishizawa et al. | ............ | 204/425 |
| 5,098,549 A * | 3/1992 | Friese et al. | .................. | 204/425 |
| 5,236,569 A * | 8/1993 | Murase et al. | ................ | 204/412 |
| 6,033,544 A * | 3/2000 | Demers et al. | ................ | 204/450 |
| 2003/0155239 A1* | 8/2003 | Stahl et al. | .................... | 204/424 |
| 2003/0164023 A1* | 9/2003 | Gruenwald et al. | ......... | 73/23.31 |
| 2004/0084309 A1* | 5/2004 | Ando et al. | .................... | 204/426 |
| 2004/0227087 A1* | 11/2004 | Markham et al. | ........ | 250/339.08 |

FOREIGN PATENT DOCUMENTS

DE 100 35 036 11/2001

(Continued)

OTHER PUBLICATIONS

Hans-Martin Wiedenmann et al., "Exhaust Gas Sensors," *Automotive Electronics Handbook*, 2nd ed., Ronald K. Jurgen (ed), McGraw-Hill (1999) pp. 6.1-6.25.
U.S. Appl. No. 60/451,484, filed Mar. 3, 2003, Markham et al.

*Primary Examiner* — Mark F Huff
*Assistant Examiner* — Rashid Alam
(74) *Attorney, Agent, or Firm* — Kenyon & Kenyon LLP

(57) ABSTRACT

A sensor element is used to detect a physical property of a measuring gas, preferably to determine the oxygen content or the temperature of an exhaust gas of an internal combustion engine. The sensor element contains a first solid electrolyte layer and a second solid electrolyte layer. A first printed conductor and a second printed conductor are provided on opposite sides of the first solid electrolyte layer, the first printed conductor including a first electrode and a feed line to the first electrode, and the second printed conductor including a second electrode and a feed line to the second electrode. A third printed conductor, which includes a third electrode and a feed line to the third electrode, is provided on the second solid electrolyte layer. The second printed conductor is positioned between the third electrode and the first printed conductor.

23 Claims, 2 Drawing Sheets

FOREIGN PATENT DOCUMENTS

| | | |
|---|---|---|
| DE | 101 00 599 | 7/2002 |
| DE | 100 53 107 | 2/2003 |
| DE | 101 23 351 | 2/2005 |
| JP | 60-128348 | 7/1985 |
| JP | 7-174729 | 7/1995 |
| WO | WO01/71332 A1 * | 9/2001 ............ 27/417 |
| WO | WO 02/06811 | 1/2002 |

* cited by examiner

SENSOR ELEMENT

BACKGROUND INFORMATION

A sensor element is known, for example, from German Patent No. DE 100 35 036 or German Patent Application No. DE 101 00 599. The sensor element includes a first and a second solid electrolyte layer. A first printed conductor having a first electrode and a first feed line and a second printed conductor having a second electrode and a second feed line are provided on opposite sides of the first solid electrolyte layer. The first electrode is positioned on an outer surface of the sensor element and is in contact with the measuring gas via an open-pored protective layer. The second electrode is positioned in a measuring gas chamber introduced into the sensor element and is connected to the measuring gas via a diffusion resistor and via a gas access opening. A third printed conductor having a third electrode and a third feed line, which is attached to the first or the second solid electrolyte layer, is provided between the first and the second solid electrolyte layers. The third electrode is subjected to a reference gas and forms an electrochemical cell (Nernst cell) with an electrode (the second electrode or a fourth electrode, for example) positioned in the measuring gas chamber. The second feed line to the second electrode and the third feed line to the third electrode run next to one another in the direction of the longitudinal axis of the sensor element in one layer plane of the sensor element.

In a system of this type, it is disadvantageous that rapid oscillation of the potential at the first electrode caused by rapid changes in the oxygen partial pressure of an exhaust gas of an internal combustion engine, for example, may impair the signal of the Nernst cell. Since the pump voltage applied between the first and the second electrodes by an external circuit is regulated using the signal of the Nernst cell, and since the pump current flowing because of this pump voltage provides the measuring signal, influencing of the Nernst voltage may corrupt the measuring signal.

SUMMARY OF THE INVENTION

The sensor element according to the present invention has the advantage that corruption of the measuring signal in the event of sudden changes in the exhaust gas composition is avoided in that the third electrode is capacitively and resistively shielded from the first printed conductor by the second printed conductor.

For this purpose, the second printed conductor is applied to the first solid electrolyte layer and the third printed conductor is applied to the third solid electrolyte layer, the second printed conductor being provided between the first printed conductor and the third electrode.

The following measures have been shown to be advantageous (individually or in combination) for improving the capacitive and resistive shielding of the third electrode. The vertical projection of the second printed conductor onto the layer plane of the third printed conductor is at least 30 percent, especially advantageously at least 50 percent, wider than the third electrode in the region of the third electrode, and/or the cited projection is at least 0.2 mm, preferably at least 0.4 mm, wider than the third electrode and/or covers the third electrode completely. The region of the second printed conductor lying in the connection line between the first electrode and the third electrode is at least 30 percent, especially advantageously at least 50 percent, wider than the third electrode, and/or this region of the second printed conductor is at least 0.2 mm, preferably at least 0.4 mm, wider than the third electrode. The second feed line is at least 0.2 mm, preferably at least 0.4 mm, wider than the third feed line, the second feed line lying, in the direction of the normal line to a layer plane of the sensor element, directly above the third supply line and/or completely covering it. The width of a printed conductor is to be understood in the scope of this application as the dimension of the printed conductor in a direction perpendicular to the longitudinal axis of the sensor element and parallel to a layer plane of the sensor element.

DETAILED DESCRIPTION

Figure 1:
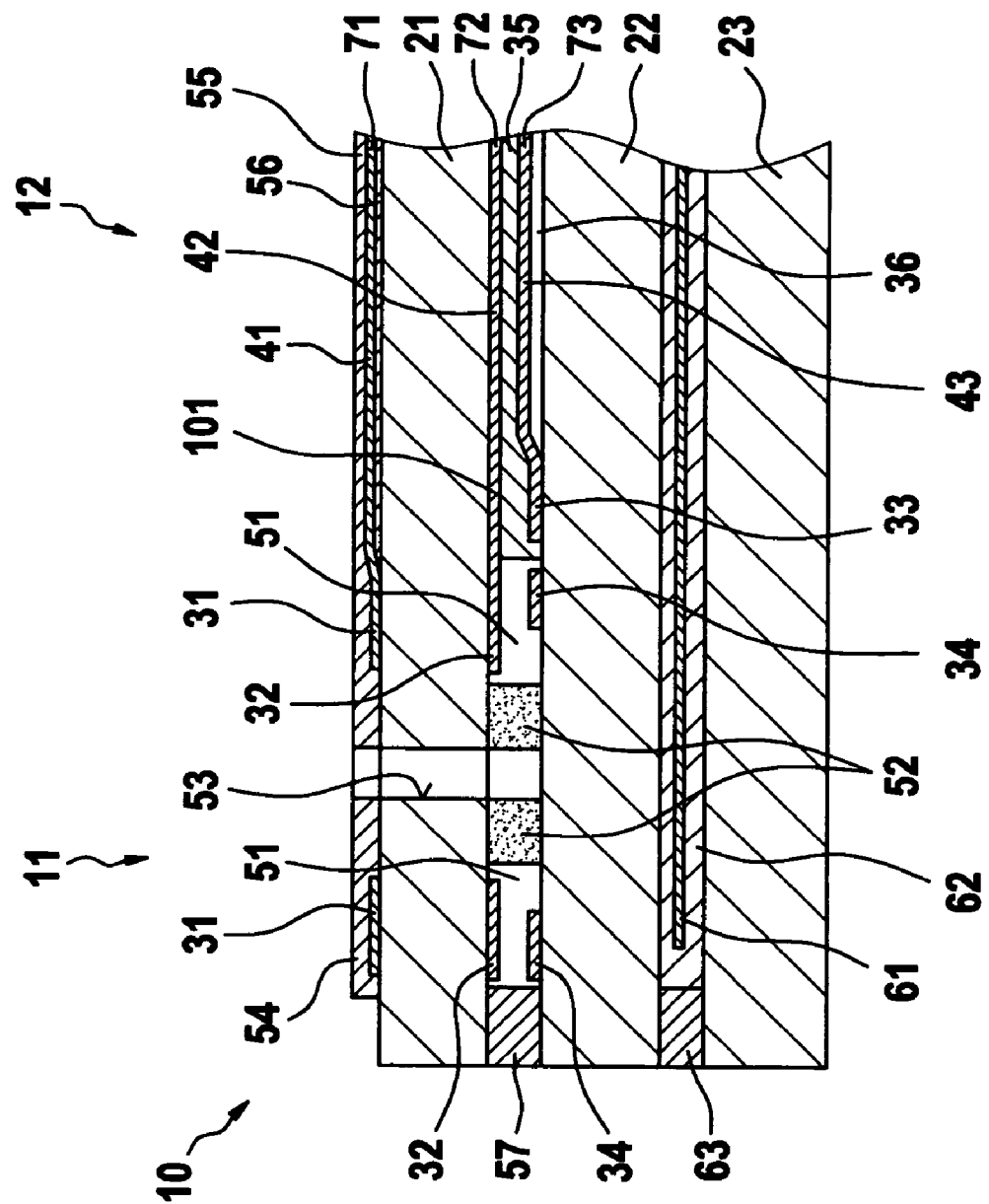
FIG. 1 shows a longitudinal section of a sensor element according to the present invention as an exemplary embodiment of the present invention.
Figure 2:
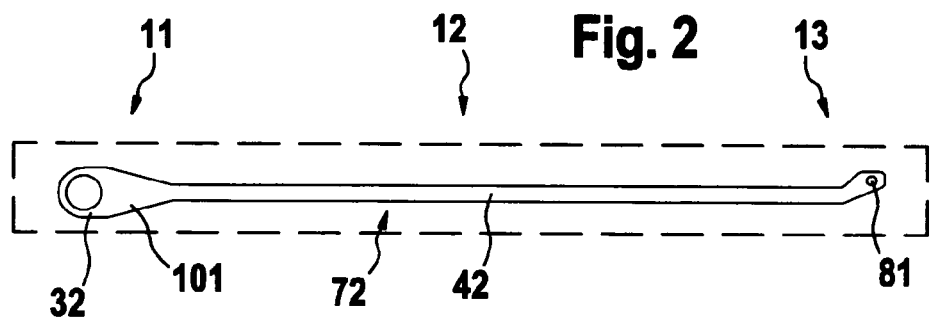
FIGS. 2 through 4 show a top view of different elements of the sensor element according to the present invention.
Figure 3:
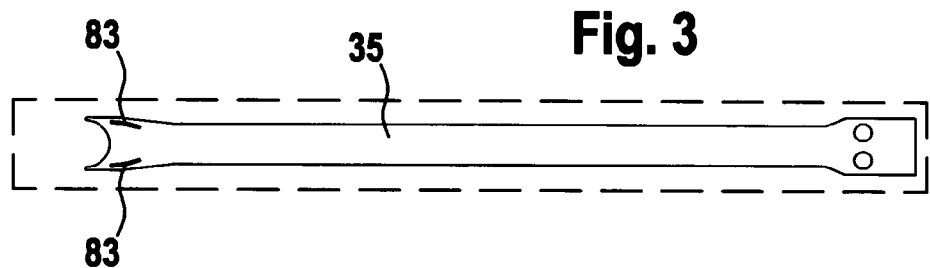
Figure 4:
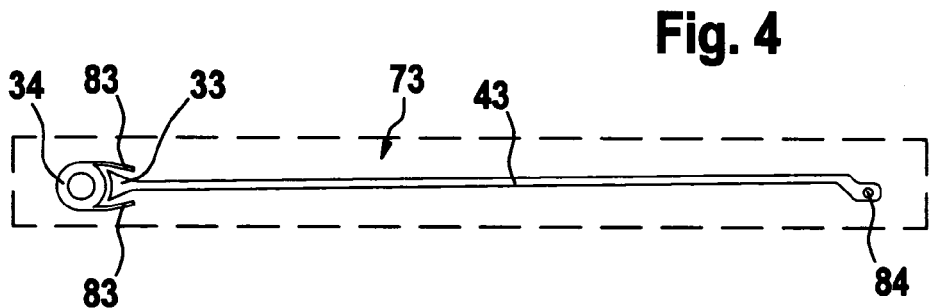

FIGS. 1 through 4 show, as an exemplary embodiment of the present invention, a sensor element 10, which has a first solid electrolyte layer 21, a second solid electrolyte layer 22, and a third solid electrolyte layer 23. A first electrode 31, to which a first feed line 41 is connected, is provided on the external surface of first electrolyte layer 21. First electrode 31 is coated by an open-pored first protective layer 54, which allows the measuring gas to access first electrode 31. First feed line 41 is covered by a second protective layer 55. First electrode 31 and first feed line 41 are assigned to a first printed conductor 71.

A gas access opening 53, which leads into a region between first and second solid electrolyte layers 21, 22, is introduced into first solid electrolyte layer 21. An annular diffusion resistor 52 is provided in this region, which is enclosed by a measuring gas chamber 51, which is also annular. Measuring gas chamber 51 is enclosed in turn by a sealing frame 57. A second electrode 32, to which a second feed line 42 is connected, is positioned on first solid electrolyte layer 21 in measuring gas chamber 51. A second printed conductor 72 includes second electrode 32, which is positioned in a measuring region 11 of sensor element 10, second feed line 42, which is positioned in a feed line region 12 of sensor element 10, and a through plating 81, which is provided in a contacting region 13 of the sensor element (see FIG. 2) and leads to a contact area (not shown) on an external surface of sensor element 10.

A third electrode 33 is provided distal from measuring gas chamber 51 on second solid electrolyte layer 22. A third feed line 43 is connected to third electrode 33. A third printed conductor 73 includes third electrode 33, third feed line 43, and a second through plating, which leads to a contact area on an external surface of sensor element 10 (see FIG. 4). A first insulation layer 35, which electrically insulates second and third printed conductors 72, 73, is provided between third printed conductor 73 and second feed line 42 and second printed conductor 72 (see FIG. 3).

A fourth electrode 34 is positioned opposite second electrode 32 on second solid electrolyte layer 22 in measuring gas chamber 51. Fourth electrode 34 has two wings 82, which electrically connect fourth electrode 34 to second printed conductor 72. Two recesses 83 are provided in first insulation layer 35 for this purpose (see FIGS. 3 and 4).

Third electrode 33 is applied directly to second solid electrolyte layer 22, while third feed line 43 is electrically insulated from second solid electrolyte layer 22 by a second insulation layer 36. First electrode 31 is also applied directly to first solid electrolyte layer 21 and first feed line 41 is insulated from first solid electrolyte layer 21 by a third insulation layer 56. Third electrode 33 has a porous design. A reference gas having a high oxygen concentration is located in the pores of third electrode 33. For this purpose, for example, porous third electrode 33 is connected to the surrounding air via an opening provided in contacting region 13 of the sensor element, or oxygen is pumped from first, second, or fourth electrode 31, 32, 34 to third electrode 33 by applying a voltage.

A heater 61, which is embedded in a heater insulation 62 and is electrically insulated from surrounding solid electrolyte layers 22, 23 by heater insulation 62, is provided between second and third solid electrolyte layers 22, 23. Heater insulation 62 is laterally enclosed by a heater sealing frame 63.

First and second electrodes 31, 32 and the region of first solid electrolyte layer 21 positioned between both electrodes 31, 32 form a first electrochemical cell, and third and fourth electrodes 33, 34 and the region of second solid electrolyte 22 positioned between both electrodes 33, 34 form a second electrochemical cell. The region of second solid electrolyte layer 22 lying between third and fourth electrodes 33, 34 refers to the region in which the field lines having a significant influence on the measuring signal of the electrochemical cell extend between third and fourth electrodes 33, 34.

The first electrochemical cell has a pump voltage applied to it by an analysis circuit positioned outside the sensor element, as is described, for example, in Automotive Electronics Handbook, second edition, edited by Ronald K. Jurgen, McGraw-Hill 1999 (see Section 6, particularly 6.2.6), the pump voltage being used to pump oxygen into measuring gas chamber 51 and/or out of measuring gas chamber 51 in such a way that an oxygen partial pressure which corresponds to the stoichiometric air-fuel ratio ($\lambda=1$) exists in measuring gas chamber 51. The pump voltage is produced using the Nernst voltage of the second electrochemical cell, the Nernst voltage being a measure of the ratio of the oxygen partial pressure existing in measuring gas chamber 51 to the oxygen partial pressure of the reference gas at third electrode 33.

Third electrode 33 broadens uniformly starting from third feed line 43 in the direction of fourth electrode 34, so that the contour of third electrode 33 approximately corresponds to a triangle. The side of third electrode 33 facing toward fourth electrode 34 is rounded in accordance with the annular contour of fourth electrode 34.

Second printed conductor 72 is broadened in a region 101 between second electrode 32 and second feed line 42. This region 101 of second printed conductor 72 is positioned over third electrode 33 and in the region of the connection line between third electrode 33 and first electrode 31. The connection line is to be understood as the line of the shortest distance between third and first electrodes 33, 31. Region 101 has a width, increasing linearly in the direction of second electrode 32 in accordance with the contour of third electrode 33, which is 0.6 mm larger than the width of third electrode 33, both in regard to the vertical projection of region 101 onto third electrode 33 and in regard to the projection along the connection line.

The present invention may also be transferred to electrodes having a different contour than the described contour of third electrode 33. According to the present invention, the second printed conductor has a greater width than the third electrode in the regions (in a layer plane between the third and the first electrodes) in which there is large capacitive and resistive coupling because of the electrical fields produced. This is the case in particular in the regions of sensor element 10 in which a high temperature exists because of the heating of measuring region 11 of sensor element 10 via heater 61.

Second and third feed lines 42, 43 run parallel to the longitudinal axis of sensor element 10 in the center of the particular large surface, the width of second and third feed lines 42, 43 being constant over the greater part of their length. Second feed line 42 is positioned directly over a third feed line 43 in relation to the normal line to the large surface of sensor element 10. Second feed line 42 has a width of 1.2 mm, and third feed line 43 has a width of 0.6 mm.

Figure 5:
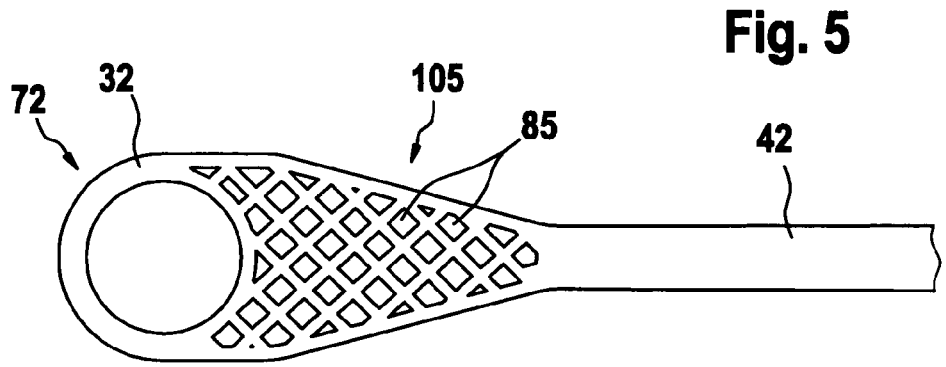
FIG. 5 shows an alternative embodiment of the element according to FIG. 2.

FIG. 5 shows an alternative embodiment of second printed conductor 72, in which second printed conductor 72 has recesses 85 in the region between second electrode 32 and second feed line 42, i.e., in widened region 101. As a result of recesses 85, second printed conductor 72 has a net-like structure in this region. Recesses 85 are advantageously designed so that the size of recesses 85 is less than or equal to the shortest distance of printed conductor 72 to printed conductor 71 in region 101. The size of recess 85 is to be understood as the diameter of the smallest circle in which recess 85 is completely contained. As a result of recesses 85, material may be saved while maintaining good resistive and capacitive shielding.

What is claimed is:

1. A sensor element comprising:
   first and second solid electrolyte layers; first and second printed conductors situated on opposite sides of the first solid electrolyte layer, the first printed conductor including a first electrode and a first feed line to the first electrode, the second printed conductor including a second electrode and a second feed line to the second electrode; and
   a third printed conductor situated on the second solid electrolyte layer, the third printed conductor including a third electrode and a third feed line to the third electrode,
   wherein the second printed conductor is situated between the third electrode and the first printed conductor, the second printed conductor being wider than the third electrode and the second feed line being wider than the third feed line to capacitively and resistively shield the third electrode from the first printed conductor.

2. The sensor element according to claim 1, wherein the sensor element is for detecting a physical property of a measuring gas.

3. The sensor element according to claim 1, wherein the sensor element is for determining an oxygen content of an exhaust gas of an internal combustion engine.

4. The sensor element according to claim 1, wherein the sensor element is for determining a temperature of an exhaust gas of an internal combustion engine.

5. The sensor element according to claim 1, wherein a region of the second printed conductor which, upon vertical projection onto a layer plane of the third printed conductor, lies on the third electrode, is at least 30 percent wider than the third electrode.

6. The sensor element according to claim 5, wherein the region is at least 50 percent wider than the third electrode.

7. The sensor element according to claim 1, wherein a region of the second printed conductor lying in a connection line between the third electrode and the first electrode is at least 30 percent wider than the third electrode.

8. The sensor element according to claim 7, wherein the region is at least 50 percent wider than the third electrode.

9. The sensor element according to claim 1, wherein a vertical projection of the second printed conductor onto a layer plane of the third printed conductor completely covers the third electrode.

10. The sensor element according to claim 1, wherein a vertical projection of the second printed conductor onto a layer plane of the third printed conductor in a region of the third electrode is at least 0.2 mm wider than the third electrode.

11. The sensor element according to claim 10, wherein the vertical projection is at least 0.4 mm wider than the third electrode.

12. The sensor element according to claim 1, wherein a projection of the second printed conductor onto the third electrode along a connection line between the third electrode and the first electrode is at least 0.2 mm wider than the third electrode.

13. The sensor element according to claim 12, wherein the projection is at least 0.4 mm wider than the third electrode.

14. The sensor element according to claim 1, wherein the second feed line is at least 0.2 mm wider than the third feed line and lies directly over the third feed line in a direction perpendicular to a layer plane of the sensor element.

15. The sensor element according to claim 14, wherein the second feed line is at least 0.4 mm wider than the third feed line.

16. The sensor element according to claim 1, wherein the second feed line, in vertical projection onto a layer plane of the third printed conductor, completely covers the third feed line.

17. The sensor element according to claim 1, further comprising an insulation layer situated between the second and third printed conductors.

18. The sensor element according to claim 1, further comprising a heater for heating a measuring region of the sensor element situated between the second solid electrolyte layer and a third solid electrolyte layer, the heater being electrically insulated from surrounding solid electrolyte layers by a heater insulation.

19. The sensor element according to claim 1, wherein the second electrode is situated in a measuring gas chamber situated between the first and second solid electrolyte layers, the measuring gas chamber being connected to the gas located outside the sensor element via a diffusion resistor and a gas access opening introduced into the first solid electrolyte layer, and further comprising a fourth electrode electrically connected to the second printed conductor and situated opposite the second electrode in the measuring gas chamber.

20. The sensor element according to claim 1, wherein the third electrode has a porous design and a reference gas is provided in pores of the third electrode.

21. A device comprising:
(a) a sensor element including:
first and second solid electrolyte layers;
first and second printed conductors situated on opposite sides of the first solid electrolyte layer, the first printed conductor including a first electrode and a first feed line to the first electrode, the second printed conductor including a second electrode and a second feed line to the second electrode; and
a third printed conductor situated on the second solid electrolyte layer, the third printed conductor including a third electrode and a third feed line to the third electrode,
wherein the second printed conductor is situated between the third electrode and the first printed conductor, the second printed conductor being wider than the third electrode and the second feed line being wider than the third feed line to capacitively and resistively shield the third electrode from the first printed conductor; and
(b) a circuit configuration situated outside the sensor element,
wherein the first and second electrodes and a region of the first solid electrolyte layer situated between the first and second electrodes form an electrochemical cell which is operable as an electrochemical pump cell by the circuit configuration.

22. The device according to claim 21, wherein the third electrode, a fourth electrode and a region of the second solid electrolyte layer situated between the third and fourth electrodes form an electrochemical cell which is operable as an electrochemical Nernst cell by the circuit configuration, an oxygen partial pressure in a measuring gas chamber being able to be determined via a Nernst voltage applied to the Nernst cell, and the circuit configuration applying a pump voltage to the pump cell in such a way that an oxygen partial pressure of $\lambda=1$ is provided in a measuring gas chamber by pumping oxygen into or out of the measuring gas chamber, the pump voltage being regulated via the Nernst voltage applied to the Nernst cell.

23. A sensor element comprising:
first and second solid electrolyte layers; first and second printed conductors situated on opposite sides of the first solid electrolyte layer, the first printed conductor including a first electrode and a first feed line to the first electrode, the second printed conductor including a second electrode and a second feed line to the second electrode; and
a third printed conductor situated on the second solid electrolyte layer, the third printed conductor including a third electrode and a third feed line to the third electrode,
wherein the second printed conductor is situated between the third electrode and the first printed conductor, the second printed conductor being wider in a direction perpendicular to a longitudinal axis of the sensor element and parallel to a layer plane of the sensor element than the third electrode and the second feed line being wider than the third feed line to capacitively and resistively shield the third electrode from the first printed conductor.

* * * * *